(12) United States Patent
Ledee et al.

(10) Patent No.: US 10,180,438 B2
(45) Date of Patent: *Jan. 15, 2019

(54) KIT FOR PREDICTING IMPLANTATION SUCCESS IN ASSISTED FERTILIZATION

(71) Applicant: FEMALON S.P.R.L., Bierset (BE)

(72) Inventors: Nathalie Ledee, Poissy (FR); Marie-Pierre Piccinni, Florence (IT)

(73) Assignee: FEMALON S.P.R.L., Bierset (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/597,617

(22) Filed: May 17, 2017

(65) Prior Publication Data

US 2018/0088125 A1    Mar. 29, 2018

Related U.S. Application Data

(60) Division of application No. 14/927,264, filed on Oct. 29, 2015, now Pat. No. 9,664,692, which is a continuation of application No. 13/539,660, filed on Jul. 2, 2012, now Pat. No. 9,176,145, which is a continuation-in-part of application No. 12/374,472, filed as application No. PCT/EP2007/057430 on Jul. 18, 2007, now Pat. No. 8,211,650.

(60) Provisional application No. 60/832,094, filed on Jul. 21, 2006.

(51) Int. Cl.
*G01N 33/68* (2006.01)
*C12Q 1/6876* (2018.01)
*C12Q 1/6883* (2018.01)

(52) U.S. Cl.
CPC ......... *G01N 33/689* (2013.01); *C12Q 1/6876* (2013.01); *C12Q 1/6883* (2013.01); *G01N 33/6863* (2013.01); *C12Q 2600/106* (2013.01); *C12Q 2600/158* (2013.01); *G01N 2333/535* (2013.01); *G01N 2800/367* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,147,902 A | 9/1992 | Ichikawa et al. | |
| 5,798,274 A | 8/1998 | Ichikawa et al. | |
| 5,849,883 A | 12/1998 | Boone et al. | |
| 7,456,288 B2 | 11/2008 | Rao et al. | |
| 7,923,251 B2 | 4/2011 | Vankov et al. | |
| 8,211,650 B2 | 7/2012 | Lédée et al. | |
| 9,176,145 B2 | 11/2015 | Lédée et al. | |
| 2016/0047818 A1 | 2/2016 | Lédée et al. | |

FOREIGN PATENT DOCUMENTS

| | | |
|---|---|---|
| JP | 2000-513208 | 10/2000 |
| JP | 2005-506317 | 3/2005 |
| WO | WO 97/30175 | 8/1997 |
| WO | WO 03/006501 | 1/2003 |

OTHER PUBLICATIONS

Giavedoni, "Simultaneous Detection of Multiple Cytokines and Chemokines from Nonhuman Primates using Luminex Technology," Journal of Immunological Methods, vol. 301, No. 1-2, pp. 89-101, Jun. 2005.
Revelli, et al. "Follicular Fluid Content and Oocyte Quality: From Single Biochemical Markers to Metabolomics," Reproductive Biology and Endocrinology, vol. 7, published online May 4, 2009, 13 pages, downloaded from http://www.ncbi.nlm.nih.gov/pmc/articles/PMC2685803/.
Salmassi, et al. "Detection of Granulocyte Colony-Stimulating Factor and Its Receptor in Human Follicular Lueteinized Granulosa Cells," Fertility and Sterility, vol. 81, Suppl. 1, pp. 786-791, Mar. 2004.
Salmassi, et al. "Is Granulocyte Colony-Stimulating Factor Level Predictive for Human IVF Outcome?, " Human Reproduction, vol. 20, No. 9, pp. 2434-2440, Sep. 2005.
Salmassi, et al. "Success of COH and IVF Correlated with Granulocyte-Colony-Stimulating Factor," Human Reproduction, vol. 21, No. Suppl. 1, p. 1159, Jun. 2006.
Wang, "Proteomic Identification of Inflammatory Markers in Cerebrospinal Fluid from in Infectious and Non-Infectious Human Brain Diseases," Society for Neuroscience Abstract Viewer and Itinerary Planner, vol. 2003, pp. Abstract No. 105.3, 2003.
Yanagi, et al. "Cyclic Changes of Granulocyte Colony-Stimulating Factor (G-CSF) mRNA in the Human Follicle During the Normal Menstrual Cycle and Immunolocalization of G-CSF Protein," Human Reproduction, vol. 17, No. 12, pp. 3046-3052, Dec. 2002.

*Primary Examiner* — James S Ketter
(74) *Attorney, Agent, or Firm* — Knobbe Martens Olson & Bear LLP

(57) ABSTRACT

A method is described to obtain a class of embryos having a higher implantation potential than from morphology selection alone by selecting from a plurality of embryos, obtained by fertilizing the plurality of oocytes, a class of embryos having a high implantation potential. The selection is determined from a level of granulocyte-colony stimulating factor (G-CSF) present in the follicular fluid (FF) of each oocyte in the plurality of oocytes.

5 Claims, 3 Drawing Sheets

KIT FOR PREDICTING IMPLANTATION SUCCESS IN ASSISTED FERTILIZATION

This application is a divisional of U.S. application Ser. No. 14/927,264, filed Oct. 29, 2015 which is a continuation of U.S. application Ser. No. 13/539,660, filed Jul. 2, 2012, now U.S. Pat. No. 9,176,145 which is a continuation-in-part of U.S. application Ser. No. 12/374,472, filed Jan. 20, 2009, now U.S. Pat. No. 8,211,650 which is incorporated herein by reference and which is the U.S. National Phase under 35 U.S.C. § 371 of International Application PCT/EP2007/057430, filed Jul. 18, 2007, which claims priority to U.S. Provisional Application No. 60/832,094, filed Jul. 21, 2006.

Assisted fertilization, such as in vitro fertilization (IVF) or intracytoplasmic sperm injection (ICSI) has been used in human patients with infertility problems successfully for three decades. Despite extensive research it is still a difficult and expensive procedure and a low implantation rate per transferred embryos (15-20%) is generally observed.

Hospitals and private centers providing an assisted fertilization service, base their selection after fertilization of the oocyte on characteristics of the embryo so produced. For example, selection may be based on the morphology of the embryo (Guerif F et al., 2007, Hum Reprod 22(7):1973), or on the production of soluble HLA-G by the embryos (Fuzzi B, et al., 2002, Eur J Immunol. February; 32(2):311-5.). Both these techniques require interference with the embryo.

To increase the pregnancy success, the number of embryos transferred typically more than one. In Europe, it is normal practice to transfer two embryos to the uterine cavity. In the US, it is more, usually three or four embryos are transferred. The adverse effect of such a policy is to increase the number of multiple pregnancies and the subsequent related obstetrical pathologies, such as prematurity and low birth rate mainly.

Furthermore, assisted fertilisation is an expensive procedure and can also be psychologically traumatic for a patient. Surgical procedures are required to collect eggs for assisted fertilization and following fertilization, further surgery is required to implant fertilized eggs in the womb. The recipient must then wait for a period of time before it can be determined whether or not pregnancy has been established. In some cases, pregnancy may never be established despite repeated attempts and these cases represent a considerable expense to society, both in financial and human terms.

Therefore, it would be desirable to provide an assay and kit which can indicate the potential for implantation of an oocyte before fertilization, enabling the chances of successful implant of the embryo to be be maximized, and allowing indications of low success rates to be used to avoid the abovementioned trauma and costs of assisted fertilization.

FIGURE LEGENDS

Figure 1:
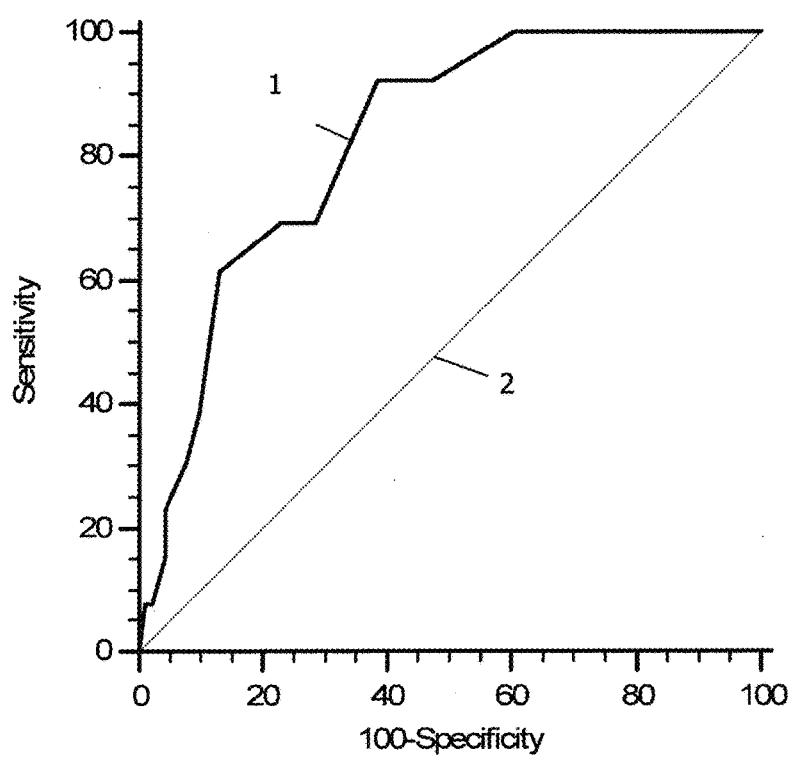

FIG. 1. ROC curve from a Luminex experiment to detect FF G-CSF using a Biorad Luminex kit. The true positive rate (Sensitivity) is plotted in function of the false positive rate (100-Specificity) for different cut-off points of FF G-CSF concentration. Each point on the ROC plot represents a sensitivity/specificity pair corresponding to a particular decision threshold. The area under the ROC curve is a measure of how well FF G-CSF can distinguish between two main diagnostic groups (certain implantation/no implantation). Line 1: The Area under curve is 0.82, indicating that a randomly selected individual from the positive group has a test value larger than that for a randomly chosen individual from the negative group in 82% of the time. Line 2: Area under the ROC curve is 0.5 representing the null hypothesis.

Figure 2:
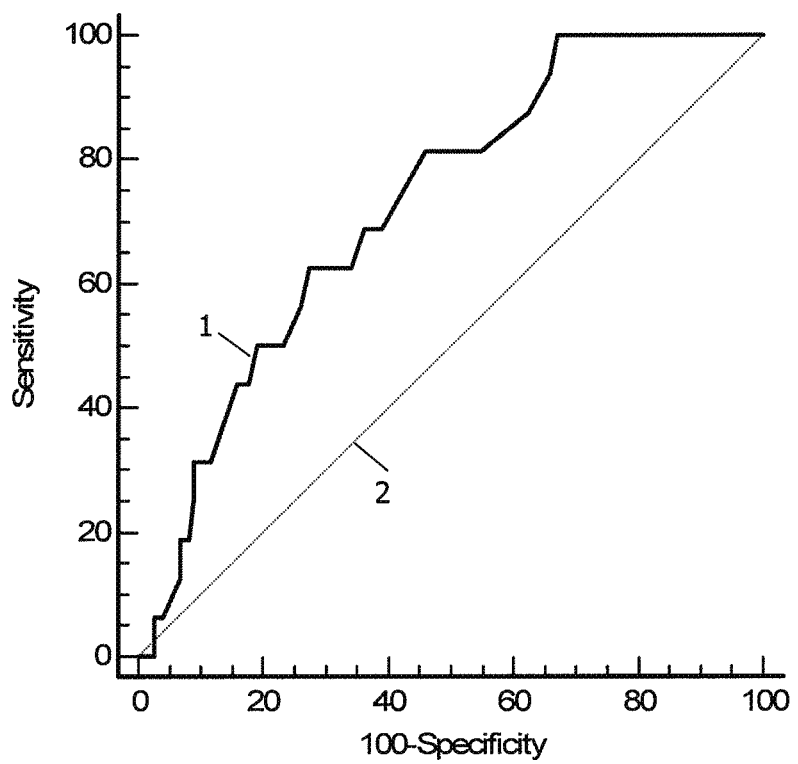

FIG. 2. ROC curve from a Luminex experiment to detect FF G-CSF using an R and D Luminex kit. Line 1: The Area under curve is 0.72, indicating that a randomly selected individual from the positive group has a test value larger than that for a randomly chosen individual from the negative group in 72% of the time. Line 2: Area under the ROC curve is 0.5 representing the null hypothesis.

Figure 3:
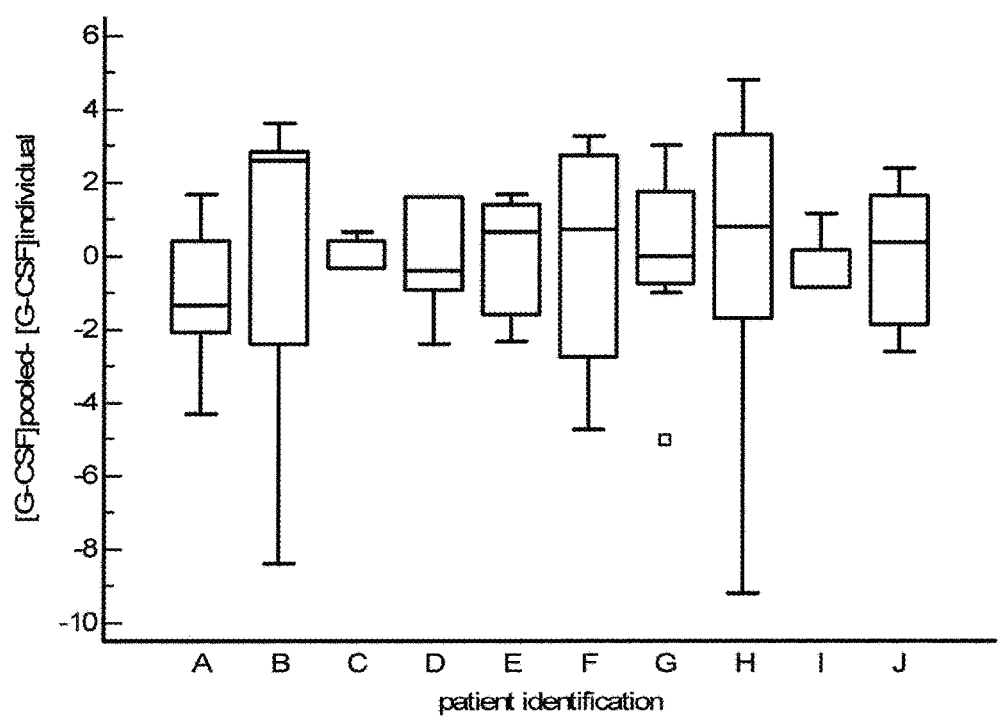

FIG. 3. Graph showing the variation in concentration of individual follicular fluid of a same cohort of embryos obtained from multiple subjects. Each box shows the variation of individual follicular fluids from the mean in a same cohort of embryos generated.

SUMMARY OF THE INVENTION

Embodiments of the invention are based on an unexpected finding by the inventors that a female subject providing a plurality of oocytes under ovarian hyperstimulation will exhibit a variation in the levels of several cytokines and growth factors present in the follicular fluid of the follicle from which each oocyte is derived. Furthermore, the inventors found there is a strong correlation between a high level of granulocyte-colony stimulating factor (G-CSF) present in the follicular fluid of the individual follicle from which an oocyte is derived and a high implantation potential of an embryo obtained by fertilization of said oocyte. It has never been demonstrated before that, for the same subject, the follicular fluid surrounding each individual oocyte may vary in composition, and that said composition is indicative of the success of implantation of the subsequently fertilized oocyte. This finding allows a plurality of embryos obtained from a single patient to be ranked in order of implantation potential. For the first time, patients showing a borderline fertility potential using indicators that average oocyte fertility markers (e.g. 11-beta HSD) may be found to have oocytes showing a high implantation potential against a poor overall average; this offer new possibilities for previously infertile-indicating females. Furthermore, the method offers the possibility to rate each oocyte individually and thus embryo individually, without interference to the embryo or oocyte.

Embodiments of the present invention relate to an assay for determining the implantation potential of a plurality of embryos each obtained or to be obtained by assisted fertilisation of an oocyte of a female subject, comprising measuring the levels of G-CSF in the follicular fluid present in the follicle from which each oocyte is derived, and determining the implantation potential of each embryo from the level of follicular fluid G-CSF. The oocyte from the follicle with the highest level of G-CSF in follicular fluid gives rise to an embryo with the greatest implantation potential.

Embodiments of the present invention relates to an assay kit which can be used to predict the outcome of assisted fertilization in a female patient. The invention also relates to such assay and kit for use in a method of fertilization treatment, to improve implantation.

One embodiment of the invention is an assay for determining for a female subject the implantation potential of embryos obtained or to be obtained by assisted fertilization comprising:
(i) measuring, for a plurality of oocytes collected from said subject, the level of follicular fluid granulocyte-colony stimulating factor (G-CSF) present in the follicular fluid (FF) of a follicle of each collected oocyte; and (ii) determining from the levels of FF G-CSF measured, the implantation potentials of the embryos obtained or to be obtained by assisted fertilization of the oocytes.

Another embodiment of the invention is an assay as described above, wherein oocytes having the highest levels of FF G-CSF have the highest potential of implantation.

Another embodiment of the invention is an assay as described above, wherein each sample of FF is obtained from a follicular aspirate.

Another embodiment of the invention is an assay as described above, wherein respective levels of FF G-CSF are measured within 20 hours of collection of the follicular aspirate.

Another embodiment of the invention is an assay as described above, wherein a level of FF G-CSF equal to or less than 20.6 pg/ml determines no or a low potential of implantation.

Another embodiment of the invention is an assay as described above, wherein a level of FF G-CSF equal to or greater than 24.0 pg/ml determines a high potential of implantation.

Another embodiment of the invention is an assay as described above, wherein the respective levels of FF G-CSF are measured using an immunoassay.

Another embodiment of the invention is an assay as described above, wherein the respective levels of FF G-CSF are measured using an a competitive or immunometric assay, such as RIA, IRMA, ELISA, or ELISPOT assay.

Another embodiment of the invention is an assay as described above, wherein the respective levels of FF G-CSF are measured using a Luminex assay.

Another embodiment of the invention is an assay as described above, wherein the Luminex assay employs a Biorad or R and D Luminex Kit.

Another embodiment of the invention is an assay as described above, wherein the respective levels of FF G-CSF are measured by determining the levels of FF G-CSF mRNA.

Another embodiment of the invention is an assay as described above, wherein the respective levels of FF G-CSF are measured by any of surface Plasmon resonance, fluorescence resonance energy transfer, bioluminescence resonance energy transfer, fluorescence quenching fluorescence, fluorescence polarization, MS, HPLC, HPLC/SM, HPLC/MS/MS, capillary electrophoresis, rod or slab gel electrophoresis.

Another embodiment of the invention is a kit for use in performing the assay as described above, comprising at least one reagent suitable for detection of levels of FF G-CSF or FF G-CSF mRNA.

Another embodiment of the invention is a kit as described above, further comprising a set of concentration standards of FF G-CSF.

Another embodiment of the invention is a kit as described above, further comprising a plurality of aspirator tips for removing an oocyte and follicular fluid from a subject.

Another embodiment of the invention is a method for assisted fertilization of a female subject comprising:
(i) collecting a plurality of oocytes from said subject,
(ii) determining the implantation potential for an embryo derived from each oocyte according to the assay as described above,
(iii) fertilizing the oocytes corresponding to embryos having a high potential for implantation, and
(iv) implanting the embryo so obtained into the female subject.

Another embodiment of the invention is a method for assisted fertilization of a female subject comprising:
(i) collecting a plurality of oocytes from said subject,
(ii) determining the implantation potential for an embryo derived from each oocyte according to the assay as described above,
(iii) fertilizing the oocytes to obtain embryos, and
(iv) implanting the embryos having a high implantation potential.

Another embodiment of the invention is a kit for determining for a female subject the implantation potential of embryos obtained or to be obtained by assisted fertilization comprising at least one reagent suitable for detection of levels of FF G-CSF or FF G-CSF mRNA. The kit may further comprise a set of concentration standards of G-CSF. The concentration standards may be commercial G-CSF standards. The kit may further comprise a plurality of aspirator tips for removing an oocyte and follicular fluid from a subject. At least one reagent may comprise an anti-G-CSF antibody for detection of levels of FF G-CSF; the anti-G-CSF antibody may be labeled. At least one reagent may comprise a nucleic acid probe for detection of levels of G-CSF mRNA; the nucleic acid probe may be labeled. The at least one reagent may comprise a specific antibody fragment, nanobody, affibody, an aptamer, a photoaptamer, a small molecule, an interacting partner, a specifically binding protein or peptide, a Darpin, or an ankyrin, an isotopically labeled tracer, or a ligand, specifically binding to said G-CSF. The specific antibody fragment may be a Fab fragment, an Fv fragment, or a scFv fragment. The at least one reagent may comprise a specific labeled antibody fragment, a labeled nanobody, a labeled affibody, a labeled aptamer, a labeled photoaptamer, a labeled small molecule, a labeled interacting partner, a labeled specifically binding protein or peptide, a labeled Darpin, a labeled ankyrin, or a labeled ligand, specifically binding to said G-CSF. The specific labeled antibody fragment may be a labeled Fab fragment, a labeled Fv fragment, or a labeled scFv fragment.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a sample" means one sample or more than one sample.

The recitation of numerical ranges by endpoints includes all integer numbers and, where appropriate, fractions subsumed within that range (e.g. 1 to 5 can include 1, 2, 3, 4 when referring to, for example, a number of samples, and can also include 1.5, 2, 2.75 and 3.80, when referring to, for example, concentrations). The recitation of end points also includes the end point values themselves (e.g. from 1.0 to 5.0 includes both 1.0 and 5.0)

As mentioned elsewhere present invention relates to an unexpected finding by the inventors that a female subject providing a plurality of oocytes under ovarian hyperstimulation will exhibit a variation in the levels of several cytokines and growth factors present in the follicular fluid of the follicle from which each oocyte is derived. Furthermore, the inventors found there is a strong correlation between a high level of granulocyte-colony stimulating factor (G-CSF) present in the follicular fluid of the individual follicle from which an oocyte is derived and a high implantation potential of an embryo obtained by fertilization of said oocyte. It has never been demonstrated before that, for the same subject, the follicular fluid surrounding each individual oocyte may vary in composition, and that said composition is indicative of the success of implantation of the subsequently fertilized oocyte. This finding allows a plurality of embryos obtained from a single patient to be ranked in order of implantation potential. For the first time, patients showing a borderline fertility potential using indicators that average oocyte fertility markers (e.g. 11-beta HSD) may be found to have oocytes showing a high implantation potential against a poor overall average; this offer new possibilities for previously infertile-indicating females. Furthermore, the method offers the possibility to rate each oocyte individually and thus embryo individually, without interference to the embryo or oocyte.

Embodiments of the present invention thus relate to an assay method and assay kit which can be used to predict the outcome of assisted fertilization in a female patient. Embodiments of the invention also relate to such assay and kit for use in a method of fertilization treatment, to improve implantation. Although our invention described below has been developed from research on human female patients, it will be applicable to any mammalian female and can be used to increase the success of, for example, captive breeding programs of endangered species or commercial breeding by assisted fertilization of livestock such as cattle or horses. Preferably the subject has undergone fertility pretreatment (e.g. ovarian hyperstimulation) to increase the number of eggs produced per monthly cycle. Assisted fertilization, as used herein, refers to ex vivo fertilization methods where the oocyte is fertilized outside the female body, such as in vitro fertilization (IVF) or intracytoplasmic sperm injection (ICSI).

One embodiment of the invention is an assay for determining the implantation potential of a plurality of embryos each obtained or to be obtained by assisted fertilisation of an oocyte of a female subject, comprising measuring the levels of G-CSF in the follicular fluid present in the follicle from which each oocyte is derived, and determining the implantation potential of each embryo from the level of follicular fluid G-CSF.

Another embodiment of the present invention is an assay for determining for a female subject the implantation potential of embryos obtained or to be obtained by assisted fertilisation comprising:
(i) measuring, for a plurality of oocytes collected from said subject, the level of follicular fluid granulocyte-colony stimulating factor (G-CSF) present in the follicular fluid (FF) of a follicle of each collected oocyte; and
(ii) determining from the levels of FF G-CSF measured, the implantation potentials of the embryos obtained or to be obtained by assisted fertilization of the oocytes.

The oocyte from the follicle with the highest level of G-CSF in follicular fluid gives rise to an embryo with the greatest implantation potential.

Granulocyte colony stimulating factor (G-CSF) is a naturally generated cytokine belonging to the family of hemopoietic growth factor (Clark, et al., 1987, Science 236(4806):1229). Its main role described is to act on proliferation, differentiation, and activation of hematopoietic cells of the neutrophilic lineage (Mielcarek et al., 1996, Blood 87(2):574, Visani et al., 1995, 18(5-6):423). Primarily produced by hemopoietic cells, G-CSF is also produce by non-hemopoietic cells, such as in the reproduction tract: the human luteinized follicular granulosa cells (Salmassi A, et al, 2004, *Fertil Steril*, 81 Suppl 1:786), endometrial cells (Giacomini G, et al., 1995, Hum Reprod 10(12):3259), decidua and placenta (Duan J. S., 1990, *Osaka City Med J* 36(2):81; Miyama M et al., 1998, *Osaka City Med J.*, 44(1):85) and various fetal tissue (Calhoun et al., 1999. Pediatr Res 46(3):333). In the ovary, G-CSF protein and its receptor were located (western blot and immunohistochemistry) mainly in granulosa cells of the follicle and luteal cells (Salmassi, et al., 2004).

The level of follicular fluid G-CSF (FF G-CSF) is preferably measured within the day of oocyte collection. As is known to the skilled person, follicular aspiration is guided using transvaginal sonography after local or general anesthesia. Each follicular fluid corresponding to one ovarian follicle visualized through vaginal sonography is aspirated individually. The capture of each oocyte does not require any other manipulation because the follicular fluid, which surrounds the oocyte, is aspirated along with the oocyte. Inspection of the follicular fluid under microscope allows immediate identification of the presence of the oocyte. Instead of pooling the follicular fluids and respective oocytes, the oocyte is separated at the time of collection so the levels of FF G-CSF can be individually measured. According to one aspect of the invention, the level of FF G-CSF is measured with 1, 2, 3, 4, 5, 6, 7, 8, 9, 10, 11, 12, 13, 14, 15, 16, 17, 18, 19, 20 hours of oocyte collection, of within a time between any two of the aforementioned values. Preferably the level of FF G-CSF is measured within 1 to 20 hours of oocyte collection.

The level of FF G-CSF associated with an oocyte can be measured using any suitable quantitative assay. The measuring may be performed, for example, using a method selected from biochemical assay (e.g., solid or liquid phase immunoassay), surface plasmon resonance, fluorescence resonance energy transfer, fluorescence quenching, and fluorescence polarization. Such techniques are well known in the art and are briefly described herein below.

Biochemical assays generally rely on the immobilization of an analyte component, for example, to a membrane or other solid support, and exposure to a ligand. After washing away excess ligand, bound ligand is detected by immunoassay, or by using labeled ligand (e.g., radio-labeled ligand, fluorescently labeled ligand, particulate labeled ligand etc.). Methods to determine and obtain ligands which bind with high affinity to a specific analyte in are also available in the art; see for example WO89/09088 entitled "Paralog Affinity Chromatography". In an example of an immunoassay, antibodies against G-CSF may be immobilized onto magnetic beads and exposed to a sample of follicular fluid. Bound G-CSF can be detected using primary and secondary antibody immunoassays to arrive at a concentration. Typically, an immunoassay is calibrated used a set of standards. Solid phase immunoassays are described for example in U.S. Pat. No. 4,376,110. Variations of the immunoassays within the scope of the invention include any competitive or immunometric assay format using anti-G-CSF antibodies, for instance RIA (radio-immunoassay), ELISA (enzyme-linked immunosorbent assay), ELISPOT (enzyme-linked immunosorbent spot) or Luminex (bead-based multiplex sandwich immunoassay).

The levels FF G-CSF are preferably measured by using Luminex technology. Luminex is a highly sensitive method for measuring simultaneously the levels of specific components in a system. It makes use of solid phase, colour (dye)

coded microspheres that are small enough to behave almost as a solution in a liquid. Each microsphere is coated with an antibody, or other ligand-binding reagent specific for the detected components (e.g. FF G-CSF). The components of the sample are captured and detected on the microspheres. Within an analyzer, lasers excite the internal dyes that identify each microsphere particle, and also any reporter dye captured during the assay. Many readings are made on each bead set, to validate the results. In this way, a sensitive multiplex assay is made that is both rapid and precise. Preferably, the levels of FF G-CSF are measured using a kit(s) manufactured by Biorad® or R and D®. In a preferred embodiment the Biorad® kit is the Human Cytokine Fluorescent Bead Immunoassay Assay Kit, Bio-Plex™ (Hercules, Calif., USA, 17A11127). In another preferred embodiment, the R and D kit is the LUH000, LUH279, LUH270, LUH271, LUH278, LUH208, LUH214, LUH215B, LUH285, LUH200, LUH280, LUH201, LUH202, LUH204, LUH205, LUH206, LUH217, LUH317, LUH210, LUH293, LUB000, LUB320, LUB294, LUB219, and/or LUB213 kit.

For the purposes of this invention, the term "antibody", unless specified to the contrary, includes monoclonal antibodies, polyclonal antibodies, and fragments of whole antibodies which retain their binding activity for a target antigen. Such fragments include Fv, F(ab') and F(ab')2 fragments, as well as single chain antibodies. Furthermore, the antibodies and fragments thereof may be humanized antibodies, e.g. as described in EP-A-239400 (Winter).

Antibodies against FF G-CSF may be monoclonal or polyclonal antibodies. Monoclonal antibodies may be prepared by conventional hybridoma technology using the proteins or peptide fragments thereof, as an immunogen. Polyclonal antibodies may also be prepared by conventional means which comprise inoculating a host animal, for example a rat or a rabbit, with a peptide of the invention and recovering immune serum.

Alternatively, levels of FF G-CSF may be estimated by analyzing the levels of FF G-CSF mRNA in the granulosa cells. Granulosa cells around the corona radiata may be stored at the stage of the decoronisation of each oocytes and be stored in RNA stabiliser (e.g. at 80° C.) until assay. Probes for the FF G-CSF gene may be designed for use as probes, for example for use in a nucleic acid (PCR) amplification assay and/or hybridization. Methods and conditions for performing a PCR and hybridization reactions are known in the art, and can be found, for example, in Molecular Cloning: A Laboratory Manual (Third Edition) (Joseph Sambrook, Peter MacCallum, David Russell, Cold Spring Habor Laboratory Press) or could be performed by a quantigene plex assay, which is designed to quantitate multiple target-specific RNA molecules (Panomics).

A surface plasmon resonance assay may, alternatively, be used as a quantitative method to measure the level of G-CSF in a follicular fluid sample. A chip-bound anti-G-CSF antibody is challenged with a follicular fluid and the surface plasmon resonance measured. Binding reactions are performed using standard concentrations to arrive at the levels of G-CSF of G-CSF in the follicular fluid.

FRET (fluorescence resonance energy transfer) may also be used to measure the level of G-CSF in a follicular fluid sample. The G-CSF and anti-G-CSF antibody are labeled with a complementary pair of donor and acceptor fluorophores. While bound closely together by the G-CSF:anti-G-CSF antibody interaction, the fluorescence emitted upon excitation of the donor fluorophore will have a different wavelength than that emitted in response to that excitation wavelength when the G-CSF and anti-G-CSF antibody are not bound, providing for quantitation of bound versus unbound molecules by measurement of emission intensity at each wavelength. Binding reactions can be compared with a set of standards to arrive at the level of G-CSF in the follicular fluid.

BRET (bioluminescence resonance energy transfer) may also be used to measure the level of G-CSF in a follicular fluid sample. Light is emitted by an acceptor when in close proximity to the donor, i.e., when a G-CSF: anti-G-CSF antibody interaction complex is formed. By comparing the interaction with a set of standards, the level of G-CSF in the follicular fluid is determined.

Fluorescence quenching fluorescence similarly provides a measurement of G-CSF levels. Generally, a decrease in fluorescence of the labeled anti-G-CSF antibody is indicative that the G-CSF bearing the quencher has bound. Of course, a similar effect would arise when a G-CSF is fluorescently labeled and anti-G-CSF antibody bears the quencher. By comparing the interaction with a set of standards, the level of G-CSF in a follicular fluid sample can be measured.

Fluorescence polarization measurement can also determine the level of G-CSF in a follicular fluid sample. Complexes, such as those formed by G-CSF associating with a fluorescently anti-G-CSF antibody, would have higher polarization values than uncomplexed, labelled anti-G-CSF antibody. This form the basis for determining the levels of G-CSF in a follicular fluid sample, which measurements are typically performed concurrent with a set of standard G-CSF concentrations.

Other methods that can be used for quantitatively assaying G-CSF in the FF include mass spectrometry (MS), high performance liquid chromatography (HPLC), HPLC/MS, HPLC/MS/MS, capillary electrophoresis and rod or slab gel electrophoresis associated with image analysis. Such techniques are well known in the art as described, for example, in *Modern HPLC for Practicing Scientists* (Dong, M, Wiley-Interscience, June 2006), *Tandem Mass Spectrometry* (McLafferty F. W. John Wiley & Sons Inc, November, 1983), *Mass Spectrometry for Biotechnology* (Siuzdak, G., Academic Press, February 1996), *Clinical Applications of Capillary Electrophoresis* (Methods in Molecular Medicine) (Palfrey S. M., Humana Press, June 1999), *Handbook of Capillary Electrophoresis, Second Edition*, (Landers J. P. CRC; December 1996), *High-Resolution Electrophoresis and Immunofixation: Techniques and Interpretation* (Keren, D. F. Hodder Arnold, January, 1994).

Once the levels of FF G-CSF have been measured in a plurality of oocytes from a single patient, the results may be used to establish the relative implantation potential of embryos obtained by fertilization of said oocytes i.e. a ranking order. The level of FF G-CSF may be used to determine whether all, some or none of the oocytes will after fertilization establish implantation in a female subject undergoing assisted fertilization treatment. In addition, the level of FF G-CSF may be used to determine whether all, some or none of the embryos will implant in a female subject undergoing assisted fertilization treatment.

In our studies, we have measured levels of FF G-CSF using immunoassays, in particular using Luminex technology from Biorad and R&D. We have found that those embryos derived from oocytes having a concentration of FF G-CSF equal to or less than 20.0 pg/ml show a reduced or no implantation success. In contrast, embryos derived from oocytes having a concentration of FF G-CSF above 24 pg/ml show a certain implantation.

Those of skill in the art will appreciate that although in our research we have determined a "threshold" level of FF G-CSF below which embryos are not implanted (and above which patients have significantly improved probability of implantation), the value is a statistical measure and other measurements and thresholds can be used. In practicing the invention, it is most important to achieve consistency of assay, and so each individual practitioner (or assisted fertilization team) will be capable of establishing their own particular assay method and determining their own threshold level. This could be established by first conducting a historical study on samples from previous patients.

Thus, the level of FF G-CSF mentioned above represents the measure we have used in our studies as a suitable limit. However, if levels of FF G-CSF were to be measured in any of the other ways mentioned above, it would be desirable to conduct, using routine procedures, a control using our method of assay in order to determine the relationship between our results and the results of other methods, in order to make direct comparisons.

According to one aspect of the invention, an embryo derived from an oocyte where a level of FF G-CSF in its follicle is equal to or less than 21.6 pg/ml, 21.4 pg/ml, 21.2 pg/ml, 21.0 pg/ml, 20.8 pg/ml, 20.6 pg/ml, 20.4 pg/ml, 20.2 pg/ml, 20.0 pg/ml, 19.8 pg/ml, 19.6 pg/ml, 19.4 pg/ml, 19.2 pg/ml, 19.0 pg/ml, 18.8 pg/ml, 18.6 pg/ml, 18.4 pg/ml, 18.2 pg/ml, 18.0 pg/ml 17.8 pg/ml, 17.6 pg/ml, 17.4 pg/ml, 17.2 pg/ml, 17.0 pg/ml, 16.8 pg/ml, 16.6 pg/ml, 16.4 pg/ml, 16.2 pg/ml, 16.0 pg/ml, 15.8 pg/ml, 15.6 pg/ml, 15.4 pg/ml, 15.2 pg/ml, 15.0 pg/ml or a level between any two of the aforementioned values, is predicted to have a low implantation potential. Preferably, a level of FF G-CSF equal to or less than 15.0 pg/ml to 20.0 pg/ml, more preferably equal to or less than 19.8 to 20.6 pg/ml, most preferably less than 20.6 pg/ml is predicted to have no or a low implantation potential. The levels of this embodiment are considered threshold levels for a method of assisted fertilization (below). A low level of implantation is a probability of implantation of 10%, 9%, 8% or less.

According to one aspect of the invention, an embryo derived from an oocyte where a level of FF G-CSF in its follicle is equal to or less than 34.0 pg/ml, 33.5 pg/ml, 33.0 pg/ml, 32.5 pg/ml, 32.0 pg/ml, 31.5 pg/ml, 31.0 pg/ml, 30.5 pg/ml, 30.0 pg/ml, 29.5 pg/ml, 29.0 pg/ml, 28.5 pg/ml, 28.0 pg/ml, 27.5 pg/ml, 27.0 pg/ml, 26.5 pg/ml, 26.0 pg/ml, 25.5 pg/ml, 25.0 pg/ml, 24.5 pg/ml, 24.0 pg/ml, 23.5 pg/ml, 23.0 pg/ml, 22.5 pg/ml, 22.0 pg/ml, 21.5 pg/ml, 21.0 pg/ml, 20.5 pg/ml, 20.0 pg/ml, 19.5 pg/ml, 19.0 pg/ml, 18.5 pg/ml, 18.0 pg/ml, 17.5 pg/ml, 17.0 pg/ml, 16.5 pg/ml, 16.0 pg/ml, 15.5 pg/ml, 15.0 pg/ml or a level between any two of the aforementioned values, is predicted to have a likely implantation success. Preferably, a level of FF G-CSF in the range 15.0 pg/ml to 34.0 pg/ml, more preferably in the range 20.0 to 24.0 pg/ml predicted to be likely to be implanted. Likely to be implanted means a higher chance of success that no certainty of implantation; a likely potential of implantation means a probability of implantation of 15% to 25%. The levels of this embodiment are considered threshold levels for a method of assisted fertilization (below).

According to one aspect of the invention, an embryo derived from an oocyte where a level of FF G-CSF in its follicle is equal to or higher than 22.0 pg/ml, 22.1 pg/ml, 22.2 pg/ml, 22.3 pg/ml, 22.4 pg/ml, 22.5 pg/ml, 22.6 pg/ml, 22.7 pg/ml, 22.8 pg/ml, 22.9 pg/ml, 23.0 pg/ml, 23.1 pg/ml, 23.2 pg/ml, 23.3 pg/ml, 23.4 pg/ml, 23.5 pg/ml, 23.6 pg/ml, 23.7 pg/ml, 23.8 pg/ml, 23.9 pg/ml, 24.0 pg/ml, 24.1 pg/ml, 24.2 pg/ml, 24.3 pg/ml, 24.4 pg/ml, 24.5 pg/ml, 24.6 pg/ml, 24.7 pg/ml, 24.8 pg/ml, 24.9 pg/ml, 25.0 pg/ml, 25.1 pg/ml, 25.2 pg/ml, 25.3 pg/ml, 25.4 pg/ml, 25.5 pg/ml, 25.6 pg/ml, 25.7 pg/ml, 25.8 pg/ml, 25.9 pg/ml, 26.0 pg/ml, 26.1 pg/ml, 26.2 pg/ml, 26.3 pg/ml or a level between any two of the aforementioned values, is predicted to have a high implantation potential. Preferably, a level of FF-CSF equal to or higher than 24.0 pg/ml, more preferably higher than 35 pg/ml is predicted to have a high implantation potential. The levels of this embodiment are considered threshold levels for a method of assisted fertilization (below). A high level of implantation is a probability of implantation of 30%, 35%, 40%, 43%, 44% or more.

If levels of FF G-CSF in such patients is significantly below the level associated with likely or certain implantation in all collected oocytes, then there would be a saving in time, money and stress to the patient not to undertake implantation. In such cases, it will be possible for the practitioner (or assisted fertilization clinic) to decide whether or not to even attempt a first implantation. On the other hand, if one or more oocytes indicate a high or complete certainty of implantation, these oocytes alone may be fertilized and the embryos so obtain implanted, so saving money and resources by fertilizing only those oocytes likely to become established as embryos. Alternatively, all the oocytes may be fertilized, and only those embryos derived from oocytes indicating a high or complete certainty of implantation, are implanted; this allows a higher chance of success as the indication of implantation does not necessarily correlated with chances of fertilization.

The present invention significantly increase the implantation rate while decreasing the number of embryos replaced. It also allows a specialist to become more efficient in preventing multiple pregnancies and all the related fetal and maternal morbidity. The oocyte and thus the embryo with the highest potential can be implanted implant, therefore, allows a policy of single embryo transfer while not decreasing the overall pregnancy rate.

The assay described herein may also be employed in a method of assisting the fertilization of a female subject. One embodiment of the invention is a method for assisted fertilization of a female subject comprising:
(i) collecting a plurality of oocytes from said subject,
(ii) determining the level of FF G-CSF in the follicle of each collected oocyte,
(iii) fertilizing the oocytes having the highest FF G-CSF levels, and
(iv) implanting the embryo so obtained into the female subject.

The number of oocytes subjected to further fertilization may be 1, 2, 3, 4 or 5 or more. Alternatively, 50%, 40%, 30%, 20%, or 10% of the oocytes are fertilized, which percentage have the highest levels of FF G-CSF.

Another embodiment of the invention is a method for assisted fertilization of a female subject comprising:
(i) collecting a plurality of oocytes from said subject,
(ii) determining the level of FF G-CSF in the follicle of each collected oocyte,
(iii) fertilizing the oocytes to obtain embryos,
(iv) implanting the embryos derived from oocytes having the highest FF G-CSF levels.

The number of embryos implanted may be 1, 2, 3, 4 or 5 or more. Alternatively, 50%, 40%, 30%, 20%, or 10% of the embryos are implanted, which percentage have the highest levels of FF G-CSF.

Another embodiment of the invention is a method for assisted fertilization of a female subject comprising:
(i) collecting a plurality of oocytes from said subject, (ii) determining the level of FF G-CSF in the follicle of each collected oocyte,
(iii) fertilizing the oocytes to obtain embryos,
(iv) implanting the embryos derived from oocytes having a FF G-CSF level above a predetermined threshold.

The number of embryos implanted may be 1, 2, 3, 4 or 5 or more. Alternatively, 50%, 40%, 30%, 20%, or 10% of the embryos are implanted, which percentage have the highest levels of FF G-CSF.

Another embodiment of the invention is a method for assisted fertilisation of a female subject comprising:
(i) collecting a plurality of oocytes from said subject,
(ii) determining the implantation potential for an embryo derived from each oocyte according to the assay as defined above,
(iii) fertilizing the oocytes corresponding to embryos having a high potential for implantation, and
(iv) implanting the embryo so obtained into the female subject.

Another embodiment of the invention is a method for assisted fertilization of a female subject comprising:
(i) collecting a plurality of oocytes from said subject,
(ii) determining the implantation potential for an embryo derived from each oocyte according to the assay as defined above,
(iii) fertilizing the oocytes to obtain embryos, and
(iv) implanting the embryos having the highest implantation potential.

The embodiments described above in regard of the assay apply to corresponding embodiments of the method of assisted fertilization. The threshold values are indicated elsewhere herein. The skilled person will understand that intervening steps may be present such as freezing after oocyte collection. By use of the present invention, it will be possible for assisted fertilization clinics to allocate resources more efficiently, so that patients with low levels of FF G-CSF in the follicle of a recovered oocyte who are unlikely to become pregnant by assisted fertilization treatment are not treated.

Kits for use in performing the assay of the invention may be provided. Such kits include at least one reagent useful for the detection of FF G-CSF.

Suitable reagents include one or more of a specific antibody fragment, nanobody, affibody, an aptamer, a photoaptamer, a small molecule, an interacting partner, a specifically binding protein or peptide, a Darpin, or an ankyrin, an isotopically labeled tracer, or a ligand, specifically binding to said G-CSF, optionally be linked to a label. The specific antibody fragment is a Fab fragment, an Fv fragment, or a scFv fragment.

The reagents and their preparation are well known in the art, and do not require elaboration. Nonetheless, for the sake of completeness, a brief summary of some of the reagents is provided. A nanobody is a single-domain antibody having a single monomeric variable antibody domain able to bind selectively to a specific antigen. A specifically binding nanobody may be prepared from a library of engineered nanobodies having a different binding regions, screened against a target. Phage display technology may be employed to select binding recombinant strains. Suitable construction and screening techniques are mentioned in WO 94/04678. An affibody is an engineered binding molecule having high stability and specificity, containing three alpha helices as a protein scaffold. The were first described in Nord, K; Nilsson, J; et al (1995). "A combinatorial library of an α-helical bacterial receptor domain". Prot. Eng. 8 (6): 601-608. A specifically binding affibody may be prepared from a library of engineered affibody having a different binding region, screened against a target. Phage display technology may be employed to select binding recombinant strains. A Darpin (designed ankyrin repeat proteins) is an engineered specific binding protein containing a number of repeats (e.g. 2, 3, 4, 5 6 or more) of an ankyrin subunit. A specifically binding Darpin may be prepared from a library of engineered Darpins having a different binding region, screened against a target. Phage display technology may be employed to select binding recombinant strains. Suitable construction and screening techniques are mentioned in WO 02/20565 and WO 2010/060748. Aptamers are engineered oligonucleic acid or peptide molecules typically having a scaffold and variable binding domain, that binds to a specific target molecule; as with others they may be screened against a target using phage display technology.

Suitable reagents include antibodies, or other suitable ligand-binding reagents, against FF G-CSF optionally linked to a label. Typical labels are those commonly used in immunoassay procedures, for example horse radish peroxidase. The kit may also contain standards, for examples predetermined amounts of FF G-CSF (e.g. protein or RNA) may be labeled with a detectable label. The kit may also contain disposable aspirator tips for use in extracting the oocytes and follicular fluid.

The kit may be used for the measurement of FF G-CSF for use in a method of diagnosis, prognosis, and/or assisted fertilization treatment of a female subject. The invention further provides the use of a reagent for the detection of FF G-CSF for the prognosis of the likelihood of establishing pregnancy by assisted fertilization in a female subject.

The abovementioned antibodies, fragments and variants thereof, and other suitable ligand-binding reagents, which may optionally be labeled with a detectable label, may be used for the manufacture of a diagnostic kit for use in the treatment or diagnosis of suitability for assisted fertilization.

Levels of FF G-CSF may also be assayed via analysis of the levels of FF G-CSF mRNA present in samples obtained. In order to achieve this, FF G-CSF or fragments thereof may be used as a probe to determine levels of G-CSF in the follicular fluid. Alternatively, levels of FF G-CSF may be estimated by analyzing the levels of FF G-CSF mRNA expressed in the follicular fluid or in the granulosa cells. Granulosa cells around the corona radiate may be stored at the stage of the decoronisation of each oocytes and stored in RNA stabiliser (e.g. at 80° C.) until assay. Such probes may also be formulated into kits in a manner analogous to those described for antibodies, and may contain control nucleic acids.

Probes for the FF G-CSF gene may be designed for use as probes, for example for use in a nucleic acid amplification assay.

EXAMPLES

The following non-limiting examples illustrate certain embodiments of the invention.

Example 1: Experimental Design

Patients 280 female patients presenting with infertility and included in an ICSI program were recruited between January 2005 to March 2007. The reason for inclusion in ICSI was predominantly male infertility but also previous IVF failure or previous low fertilization rate in conventional IVF. We proceeded to a randomization at the time of inclusion to not introduce biases in the clinical patient selection. Each patient was included one time within the study period. All patients were fully informed, and the Institutional Review Board approved this investigation (Comite Consultatif de Protection des personnes Poissy-St germain en Laye,).

Pre-Treatment

Patients underwent the classical procedure of ovarian hyperstimulation. We applied the protocol referred by their physician. Response to stimulation was controlled by serial blood tests and ultrasonic evaluation to control follicles and endometrial growth. Criteria for triggering the ovulation was obtained when at least 5 follicles reached 16 mm.

The oocytes retrieval took place 35 to 36 hours after the triggering of ovulation. The oocyte aspiration was performed under general or local anesthesia with vaginal ultrasonography using individual 10 ml syringe for each follicle in the studied group. We thus adapted the classical method of oocyte aspiration in order to individualize the follicular fluid of each oocyte collected.

Follicular Fluid Samples

The presence or absence of an oocyte in each follicle was immediately assessed and the follicles devoid of an oocyte were discarded. In the studied group, individual follicular fluid sample, each corresponding to one mature oocyte was collected. The volume and the aspect (citrin, orange or hematic) of each follicular fluid sample were recorded. Individual follicular fluid samples were centrifuged and the supernatant aliquoted after proceeding to the anonymisation of each sample according to a database in order to blind subsequent analysis. Samples were initially stored at −20° C., then at −80° C. until assay. All the clinical and biological information were recorded in real-time on the database (Medifirst).

Oocyte Fertilization and Embryo Culture Until Day 2

Oocytes were collected and cumuls and corona cells removed with hyluronidase 80 IU (Fertipro). Oocyte were injected in a 5 µl drop of flushing medium (JCD), with a sperm sample slowed by PVP medium (fertopto). Injected oocytes were cultured in singly 40 µl microdroplet of ISM1 (Medicult, france) under oil at 37° C. Pronuclei number and aspect were assesses after 20 hours according to Gianaroli criteria. On day 2, the number, fragmentation and regularity of each blastomere were recorded. Embryo transfer was scheduled on day 2.

We divided the transferred embryos in two categories for analysis:
1. the best quality embryos defined by 4-5 cells on Day 2, 8-9 on Day 3, and less than 10% of fragmentation and regular cells (high quality embryos), or
2. any other patterns (low quality embryos)

Only, the follicular fluids corresponding to the embryos transferred were analysed using the Luminex method.

Evaluation of the Potential of Implantation

Each sample was related to a probability of implantation, described here as the implantation rate. The clinical Implantation rate of an embryo is defined for each tested sample as the number of yolk sac/number of embryos transferred. Clinical implantation was defined at 8 weeks of amenorrhea by the ultrasonic visualization of a yolk sac.

There is therefore three main categories in function of the outcome:
No implantation: Implantation Rate=0
Certain implantation: The number of embryos replaced was equal to the number of yolk sac observed by ultrasound at 8 weeks of amenorrhea (1 embryo replaced and single pregnancy, two embryos replaced and twin pregnancy): Implantation Rate=1
Likely implantation which is a probability of implantation since the number of yolk sac is lower than the number of embryos replaced (e.g 1 out of 2, 1 out of 3, 2 out of 3, hence Implantation Rate=0.5, 0.33, 0.66).

To construct the ROC curve (Receiver Operating Characteristics), we only took in account the two categories
No implantation,
Certain implantation: The number of embryos replaced was equal to the number of yolk sac observed by ultrasound at 8 weeks of amenorrhea (1 embryo replaced and single pregnancy, two embryos replaced and twin pregnancy)

The discrimination attained between no implantation and certain implantation in function of the concentration of G-CSF in each sample was evaluated with ROC curve analysis (MedCalc Software, Mariakerke, Belgium). Sensitivity, specificity and the area under curve (AUC) ROC were obtained for the three methods of detection. In a ROC curve the true positive rate (Sensitivity) is plotted in function of the false positive rate (100-Specificity) for different cut-off points. Each point on the ROC plot represents a sensitivity/specificity pair corresponding to a particular decision threshold. A test with perfect discrimination (no overlap in the two distributions) has a ROC plot that passes through the upper left corner (100% sensitivity, 100% specificity). Therefore, the closer the ROC plot is to the upper left corner, the higher the overall accuracy of the test (Zweig & Campbell, 1993).

Calculation of the AUC-ROC provides the quantitative of accuracy, i.e. the ability of G-CSF to discriminate between implantation and no implantation.

However, most of the embryos that implant were defined by a probability of implantation. For example, if two embryos were transferred and only one implanted, each sample is characterized by a probability of 50% of implantation.

We thus defined for each method
Lower threshold of implantation defined by a negative predictive value of 100% from the AUC-ROC curve.
Higher threshold of implantation defined by the highest positive predictive value for implantation.

G-CSF Assays Performed on the FF Samples

Two Luminex methods of detection were successively applied for individual follicular fluid samples from which transferred embryos were issue.

From January, 2005 to June 2005
The Luminex technology was applied with the kit Biorad (Hercules, Ca, USA, 17A11127, human cytokines, 27-plex kit).

From September 2005 to March 2007
80 of the samples were common to the previous Luminex biorad, and 120 were new samples collected
The Luminex technology was applied with the R and D kit (Minneapolis, Minn., USA, LUH000, LUH279, LUH270, LUH271, LUH278, LUH208, LUH214, LUH215B, LUH285, LUH200, LUH280, LUH201, LUH202, LUH204, LUH205, LUH206, LUH217, LUH317, LUH210, LUH293, LUB000, LUB320, LUB294, LUB219, LUB213)

Multivariate and univariate analysis were performed. A p value below 0.05 was considered as significant. Table 1 summarizes the population and the number of samples analyzed successively using the two of the methods of investigation applied.

TABLE 1

Population and the number of samples analyzed successively using two of the methods of investigation applied.

| Parameter measured | Luminex BIORAD | Luminex R&D |
|---|---|---|
| Number of patients included | 71 | 121 |
| Number of individual follicular fluids analysed corresponding to an transferred embryo | 132 | 200 |
| Mean Clinical Pregnancy Rate | 31.5% | 27.3% |
| Mean implantation rate | 20% | 18% |

Evaluations using the Biorad® and R and D® Luminex kits are elaborated in Examples 2 and 3.

Example 2: Evaluation Using the Luminex Kit Manufactured by Biorad®

132 follicular fluid samples corresponding to the subsequent 132 transferred embryos were analyzed for levels of certain cytokines and chemokines. In particular, concentrations of IL-1beta, IL-1Ra, IL-2, IL-4, IL-5, IL-6, IL-8, IL-9, IL-10, IL-12, IL-13, IL-15, IL-17, IFN alpha, TNF-alpha, G-CSF, GM-CSF, VEGF, PDGF, FGF, IP-10, MCP-1, RANTES, EOTAXIN, MIP-1 alpha, MIP-1 beta were evaluated using Luminex technology, utilizing a a Biorad® Luminex® Kit.

The following results were obtained:

1) LIF, IL-1ra, IL-4, IL-6, IL-8, IL-10, IL-12, IL-13, G-CSF, VEGF, IP-10, MCP-1, Eotaxin and MIP-beta were detected in all the follicular fluid samples, 2) IL-1 beta, IL-5, IL-7, IL-17, TNF alpha, MIP-alpha were detected not detected in any follicular fluid sample, 3) IL-15, GM-CSF, Rantes, PDGF, IFN-gamma, IL-9, IL-2, IL-15, FGF were detected respectively in 95%, 94%, 88%, 81%, 76%, 65%, 60%, 48% and 22% of the follicular fluid samples.

G-CSF was not related to the embryo morphology if compared in regard the two categories best embryo quality versus others. Therefore, there was no correlation between G-CSF and embryo morphological quality (High quality versus other quality transferred embryos)

Cytokines, Growth Factors and Implantation Rates

Only one cytokine was associated in either univariate and multivariate analysis with the potential of the corresponding embryo to implant, which was the Granulocyte-Colony Stimulating factor (G-CSF)

Embryos were Classified According to their Implantation Rates.

To construct the AUC-ROC for G-CSF, we took into account embryos that did not implant (n=89) and the ones that exhibited implantation (n=13). Certain implantation is defined when all the embryos replaced leads to a yolk sac.

The area under the ROC curve was 0.82 [0.73-0.89] and highly significant (p=0.0001) (FIG. 1). Thus, G-CSF is correlated with the implantation rate (r=0.40 p<0.0001).

We also found a significant difference between embryos with certain implantation and no implantation (p=0.0002) and between embryos with certain implantation and likely implantation (p=0.001) (Table 2)

TABLE 2

Correlation between implantation success and levels of FF G-CSF and FF IL-1ra measured using a Luminex kit manufactured by Biorad

| Implantation | Number of embryos concerned | FF G-CSF +/− standard error (pg/ml) | FF IL-1ra +/− standard error (pg/ml) |
|---|---|---|---|
| Certain implantation | 13 | 25.3 +/− 1 | 764 +/− 373 |
| Likely implantation | 30 | 21.6 +/− 1 | 225 +/− 106 |
| No implantation | 89 | 20.2 +/− 0.4 | 148 +/− 17 |

According to the AUC-ROC curve, we defined a lower threshold and upper threshold for G-CSF to evaluate if G-CSF concentration may be used to evaluate for each embryo a "potential of implantation" in order to decide the number of embryos we should replace.

The lower threshold was defined by the stronger negative predictive value of implantation. If G-CSF is lower than 20 pg/ml, negative predictive value is at 100% from AUC-ROC. If G-CSF is over 24, positive predictive value reaches its maximum: 40%

If all the embryos replaced are evaluated according to the level of G-CSF, we can observe the subsequent differences of the implantation rate (Table 3).

TABLE 3

Correlation between implantation success and levels of FF G-CSF measured using a Luminex kit manufactured by Biorad;

| G-CSF (Luminex biorad) | Number of embryos concerned | Mean implantation rate |
|---|---|---|
| Low G-CSF (Below 20 pg/ml) | 45 | 9% |
| Medium G-CSF (Between 20 to 24 pg/ml) | 62 | 18%* |
| High G-CSF (Over 24 pg/m)l | 25 | 44%** |

*p = 0.003 between medium and low G-CSF;
**p < 0.001 between high and low G-CSF

Example 3: Evaluation of Follicular Fluids Using the Luminex Kit Manufactured by R and D 200 follicular fluid samples corresponding to the subsequent 200 transferred embryos were analyzed. The concentrations of the following cytokines and chemokines IL-1 alpha, IL-1beta, IL-1Ra, IL-2, IL-4, IL-5, IL-6, IL-8, IL-10, IL-17, IFN alpha, TNF-alpha, G-CSF, GM-CSF, MIP-1 alpha, MIP-1 beta, RANTES, MCP-1, VEGF, were evaluated using Luminex technology utilizing the kit made by R&D.

Detection of Cytokines and Chemokines

G-CSF, IL-1 Ra; IL-6, IL-8, MIP-beta, RANTES, MCP-1, VEGF were detected in 95 to 100% of the follicular fluid samples tested:

IL-4, TNF-alpha, GM-CSF, IL-5 were detected in 75% to 94% of the follicular fluid samples tested, IL-1 alpha, IL-1 beta, IL-10, MIP-alpha were detected in 50 to 74% of the follicular fluid samples tested, IL-2, IFN-gamma and IL-17 were detected in less than 50% of the follicular fluid samples tested.

Cytokines, Chemokines and Implantation Rates

To construct the AUC-ROC for G-CSF, we took in account embryos that did not implant (n=146) and the ones that certainly implanted (n=16) The area under the ROC curve was at 0.72 [0.65-0.79] and highly significant (p=0.0025) (FIG. 2)

A significant difference was observed for G-CSF between embryos with certain implantation and no implantation (p=0.01) success and between embryos with likely implantation success and certain implantation success (p=0.03) (Table 4)

TABLE 4

Correlation between implantation success and levels of FF G-CSF measured using a Luminex kit manufactured by R and D.

| Implantation | Number of embryos concerned | G-CSF(pg/ml) +/− standard error |
| --- | --- | --- |
| Certain implantation | 16 | 28 +/− 2.3 |
| Likely implantation | 37 | 20.5 +/− 1.7 |
| No implantation | 146 | 20.7 +/− 0.9 |

G-CSF was detected in all fluids and with low standard variations from a sample to another which is a strong requirement to identify a biomarker. According to the AUC-ROC curve, we defined a lower threshold and upper threshold for G-CSF to evaluate if G-CSF concentration may be used to predict for each embryo a "potential of implantation" that would help in the decision of the number of embryos we should replace. The lower threshold was defined by the stronger negative predictive value of implantation. If G-CSF is lower than 15 pg/ml, negative predictive value was 100% from AUC-ROC. If G-CSF was over 34, positive predictive value reaches it maximum of 27.8%.

If all the embryos replaced are evaluated according to level category defined by the AUC-ROC of G-CSF, we can observe the subsequent differences of the implantation potentiality (TABLE 5).

TABLE 5

Correlation between implantation success and levels of FF G-CSF measured using a Luminex kit manufactured by R and D;

| G-CSF | Number of embryos concerned | Mean implantation rate |
| --- | --- | --- |
| Low G-CSF (Below 15 pg/ml) | 61 | 9%** |
| Medium G-CSF (Between 15 to 34 pg/ml) | 117 | 22%** |
| High G-CSF (Over 35 pg/m)l | 22 | 43.5%** |

**p < 0.001 between low, median, and high G-CSF

Example 4: The Mean of G-CSF in Pooled Follicular Fluid do not Reflect the Variations Observed in Individual Follicular Fluids Among 15 patients, all the follicular fluids that lead to an embryo independently of its outcome were evaluated in the same cohort. 76 samples were evaluated using the Luminex kit manufactured by Biorad.

For each sample, we evaluated the following ratio. Mean G-CSF in pooled Follicular fluid Less G-CSF concentration in individual FF (n=76).

FIG. 3 is graph showing the variation in concentration of individual follicular fluid of a same cohort of embryos obtained from 10 multiple subjects. Each box shows the variation of individual follicular fluids from the mean in a same cohort of embryos generated. These observation suggests that all the embryos generated are not equal in regard of FF-GCSF and hence in their potential of implantation.

What is claimed is:

1. An assay comprising the steps of:
   a. obtaining a plurality of samples of follicular fluid (FF), wherein each sample of FF was collected from a separate oocyte from a subject;
   b. assaying each sample of FF for a level of granulocyte-colony stimulating factor G-CSF; and
   c. determining the level of G-CSF from each sample of FF from the plurality of samples.

2. The method of claim 1, wherein the assay is radioimmunoassay (RIA), enzyme-linked immunosorbent assay (ELISA) or enzyme-linked immunosorbent spot (ELISPOT) assay, surface plasmon resonance, fluorescence resonance energy transfer, bioluminescence resonance energy transfer, fluorescence quenching fluorescence, fluorescence polarization, mass spectrometry (MS), high performance liquid chromatography (HPLC), HPLC/MS, HPLC/MS/MS, capillary electrophoresis, rod or slab gel electrophoresis.

3. A method of producing, from a plurality of oocytes from a subject, a class of embryos having a higher implantation potential than from morphology selection alone, comprising: selecting from a plurality of embryos, obtained by fertilizing the plurality of oocytes, a class of embryos having a high implantation potential, wherein the selection is determined from a level of granulocyte-colony stimulating factor (G-CSF) present in the follicular fluid (FF) of each oocyte in the plurality of oocytes.

4. The method of claim 3, wherein said embryos having a high implantation potential have levels of G-CSF present in the FF which are equal to or greater than 24.0 pg/ml.

5. The method of claim 3, wherein said embryos having a high implantation potential have levels of G-CSF present in the FF which is greater than 35.0 pg/ml.

* * * * *

UNITED STATES PATENT AND TRADEMARK OFFICE
CERTIFICATE OF CORRECTION

PATENT NO. : 10,180,438 B2
APPLICATION NO. : 15/597617
DATED : January 15, 2019
INVENTOR(S) : Nathalie Lédée and Marie-Pierre Piccinni It is certified that error appears in the above-identified patent and that said Letters Patent is hereby corrected as shown below:

In the Specification

Column 1, Line 27, "-5.)." should be -- -5).--.
Column 1, Line 50, "be be" should be --be--.
Column 3, Line 28, "an a" should be --a--.
Column 3, Line 45, "HPLC/SM," should be --HPLC/MS,--.
Column 4, Line 61, "5.0)" should be --5.0).--.
Column 7, Line 49, "Habor" should be --Harbor--.
Column 11, Line 64, "The" should be --They--.
Column 12, Line 6 (approx.), "5" should be --5,--.
Column 13, Line 5 (approx.), "Laye,)." should be --Laye).--.
Column 13, Lines 14-20 (approx.), Delete "The oocytes retrieval took place 35 to 36 hours after the triggering of ovulation. The oocyte aspiration was performed under general or local anesthesia with vaginal ultrasonography using individual 10 ml syringe for each follicle in the studied group. We thus adapted the classical method of oocyte aspiration in order to individualize the follicular fluid of each oocyte collected." and insert the same on Column 13, Line 12 (approx.), as a continuation of the same paragraph.
Column 13, Line 36, "cumuls" should be --cumulus--.
Column 13, Line 37, "hyluronidase" should be --hyaluronidase--.
Column 13, Line 39, "(fertopto)." should be --(Fertipro).--.
Column 13, Line 41, "france)" should be --France)--.
Column 13, Line 52 (approx.), "embryos)" should be --embryos).--.
Column 14, Line 7-8, "Charateristics)," should be --Characteristics),--.
Column 14, Line 14 (approx.), "pregnancy)" should be --pregnancy).--.
Column 14, Line 55, "collected" should be --collected.--.
Column 14, Line 62, "LUB213)" should be --LUB213).--.
Column 15, Line 28 (approx.), "a a" should be --a--.
Column 15, Line 46 (approx.), "embryos)" should be --embryos).--.
Column 15, Line 49, "and" should be --or--.
Column 15, Line 52, "(G-CSF)" should be --(G-CSF).--.

Signed and Sealed this
Twenty-third Day of April, 2019

Andrei Iancu
*Director of the United States Patent and Trademark Office*

CERTIFICATE OF CORRECTION (continued)
U.S. Pat. No. 10,180,438 B2

Column 15, Line 67, "2)" should be --2).--.
Column 16, Line 21 (approx.), "40%" should be --40%.--.
Column 16, Line 36 (approx.), "pg/m)l" should be --pg/ml)--.
Column 16, Line 65, "16)" should be --16).--.
Column 16, Line 67, "2)" should be --2).--.
Column 17, Line 5 (approx.), "4)" should be --4).--.
Column 17, Line 48 (approx.) (TABLE 5), "pg/m)l" should be --pg/ml)--.
Column 18, Line 17 (approx.), "GCSF" should be --G-CSF--.

In the Claims

Column 18, Line 27, Claim 2 "method" should be --assay--.